(12) United States Patent
Kuchuk

(10) Patent No.: US 7,226,787 B2
(45) Date of Patent: Jun. 5, 2007

(54) METHODS FOR TRANSFORMING PLANT PLASTIDS AND MAKING TRANSPLASTOMIC PLANTS

(75) Inventor: Nikolay V. Kuchuk, Kiev (UA)

(73) Assignee: Icon Genetics, Inc. (DE)

( * ) Notice: Subject to any disclaimer, the term of this patent is extended or adjusted under 35 U.S.C. 154(b) by 387 days.

(21) Appl. No.: 10/239,471

(22) PCT Filed: Mar. 22, 2001

(86) PCT No.: PCT/US01/09318

§ 371 (c)(1),
(2), (4) Date: Sep. 23, 2002

(87) PCT Pub. No.: WO01/70939

PCT Pub. Date: Sep. 27, 2001

(65) Prior Publication Data

US 2003/0207452 A1 Nov. 6, 2003

Related U.S. Application Data

(60) Provisional application No. 60/191,147, filed on Mar. 22, 2000.

(51) Int. Cl.
*C12N 15/82* (2006.01)
(52) U.S. Cl. .................................................. 435/468
(58) Field of Classification Search ............... 800/278, 800/298; 435/411, 414, 419, 417, 468
See application file for complete search history.

(56) References Cited

U.S. PATENT DOCUMENTS

| | | | |
|---|---|---|---|
| 5,451,513 A | 9/1995 | Maliga et al. | |
| 5,545,818 A | 8/1996 | McBride et al. | |
| 5,693,507 A | 12/1997 | Daniell et al. | |
| 2003/0200568 A1* | 10/2003 | Maliga et al. | 800/289 |
| 2004/0237131 A1* | 11/2004 | Bock et al. | 800/278 |

FOREIGN PATENT DOCUMENTS

| | | |
|---|---|---|
| EP | 251 654 A2 | 1/1998 |
| WO | WO 95/16783 | 6/1995 |
| WO | WO 95/24492 | 9/1995 |
| WO | WO 95/24493 | 9/1995 |
| WO | WO 95/25787 | 9/1995 |
| WO | WO 97/06250 | 2/1997 |
| WO | WO 97/32977 | 9/1997 |
| WO | WO 97/47771 | 12/1997 |
| WO | WO 99/05265 | 2/1999 |
| WO | WO 00/28014 | 5/2000 |
| WO | WO 00/39313 | 7/2000 |

OTHER PUBLICATIONS

Sidorov et al, 1999, Plant J. 19:209-216.*

Koop, et al., "Integration o foreign sequences into the tobacco plastome via polyethylene glycol-mediated protoplast transformation", Planta, 1996, vol. 199, pp. 193-201.

Thanh, et al., "Limited chloroplast gene transfer via recombination overcomes plastomegenome incompatibility between *Nicotiana tabacum* and *Solanum tubersum*", plant. Mol. Biol., Jan. 1989, vol. 12, No. 1, pp. 87-93.

Wolters, et al., "Analysis if nuclear and organellar DNA of somatic hybrid calli and plants between *Lycopersicon* spp. and *nicotiana* spp.", Mol. Gen. Genet. 1993, vol. 241, pp. 707-718.

Kushnir, et al., "Functional cybrid plants possessing a *Nicotiana* genome and an *Atropa plastome*.", Mol. Gen. Genet., 1987, vol. 209, pp. 159-163.

Svab, et al., "High-frequency plastid transformation in tobacco by selection for a chimeric aadA gene", Proc. Natl. Acad. Sci. USA, Feb. 1993, vol. 90, No. 3, pp. 913-917.

Koop, et al., "Protoplasts in organelle research: Transfer and transformation of plastids", Physiol. Plant, vol. 85, No. 2, pp. 339-344.

Okamura, M., "Pomato: Potato Protoplast System and Somatic Hybridization Between Potato and a Wild Tomato", Biotechnology in Agriculture and Forestry, 1994, pp. 209-223.

Brock, A.J. Pryor, "An unstable minichromosome generates variegated oil yellow maize seedlings", Chromosoma: Biology of the Nucleus, Sep. 1995, pp. 12-21.

Dudits, Dened, Transfer of resistance traits from carrot into tobacco by asymmetric somatic hybridization: Regeneration of fertile plants., Proceedings of the National Academy of Sciences, Dec. 1987, pp. 8434-8438.

Parokonny, A.S., Genome reorganization in *Nicotiana* asymmetric somatic hybrids analysed by in situ hybridaization, The Plant Journal vol. 2, No. 6, Nov. 1992. pp. 863-874.

O'neill, C. et al, The Plant Journal: For Cell and Molecular Biology: 3:729-738 (1993).

Baldev, et al., *Mol. Gen. Genet*, 260:357-361 (1998).

Bilang, et al., Nature Biotech. 16:333-334 (1998).

Boynton, et al., *Science*, 240:1534-1537 (1988).

Carrer, et al., Molec. Gen. Genet. 241:49-56 (1993).

Daniell, et al., *BiolTechnology* 16:345-348 (1998).

Eigel, et al., *Mol. Gen. Genet*. 233:479-482 (1992).

Fahleson, et al., Theor. Appl. Genet. 87:795-804 (1994).

Gleba, et al., Monogr. Theor. Appl. Genet. 8:1-220 (1984).

Jarvis, et al., *Science* 282:100-103 (1998).

(Continued)

*Primary Examiner*—Anne Kubelik
(74) *Attorney, Agent, or Firm*—Lerner, David, Littenberg, Krumholz & Mentlik, LLP

(57) ABSTRACT

Disclosed are methods for transforming plastids and moving transformed plastids from one plant to another. Also disclosed are transplastomic plants, parts thereof, and seed derived therefrom. Further disclosed is a cell or protoplast of a plant, or a culture thereof (e.g., a callus culture) wherein the cell or protoplast contains a plastid obtained from a cell of a genetically distinct plant and that contains a nucleic acid of interest.

22 Claims, 6 Drawing Sheets

OTHER PUBLICATIONS

Kanevski, et al., Plant Physiol. 119:133-141 (1999).
Kermickle, *Science 166*:1422-1424 (1969).
Kindiger, *Crop Sci*, 34:321-322 (1994).
Kota, et al., *Proc. Natl. Acad. Sci. USA 96*:1840-1845 (1999).
Kushnir, et al., Mol. Gen. Genet. 209:159-163 (1987).
McBride, et al., Bio/Technology 13:362-365 (1995).
Ramulu, et al., *Planta 190*:190-198 (1993).
Shinozaki, et al., EMBO J. 5:2043-2049 (1986).
Sidorov, et al., Proc Academy of Sci USSR, 308:741-744(1989).
Sidorov, et al., *The Plant J. 19*:209-216 (1999).
Sidorov, et al., Theor. Appl. Genet. 88:525-529 (1994).
Sikdar, et al., Plant Cell Rep. 18:20-24 (1998).
Strepp, et al., *Proc. Natl. Acad. Sci. USA 95*:4368-4373 (1998).
Svab, et al., Proc. Natl. Acad. Sci. USA 87:8526-8530 (1990).
Thanh, et al., *Mol. Gen. Genet. 213*:186-190 (1988).
Verhoeven, et al., *Plant Cell Rep. 14*:781-785 (1995).
Zubko, et al., *J. Exp. Botany 47*:1101-1110 (1996).
Zubko, et al., *Plant J. 15*:265-271 (1998).

* cited by examiner

SEQUENCE LISTING

<160> NUMBER OF SEQ ID NOS: 8

<210> SEQ ID NO 1
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 1
ccgaattcgc cgtcgttcaa tgag                                          24

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 2
cacgatatcg cccggagttg                                               20

<210> SEQ ID NO 3
<211> LENGTH: 27
<212> TYPE: DNA
<213> ORGANISM: Artificial Sequence
<220> FEATURE:
<223> OTHER INFORMATION: Description of Artificial Sequence: Primer

```
<400> SEQUENCE: 3
ctcgatatca ctagttgtag ggaggga                                        27

<210> SEQ ID NO 4
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 4
gtgccatgga tccctcct                                                  18

<210> SEQ ID NO 5
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 5
ccacgtcaag gtgacactc                                                 19

<210> SEQ ID NO 6
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 6
ctgcagtacc tcgacgtg                                                  18

<210> SEQ ID NO 7
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 7
gctcgagata ccggtcccgg gaattcgccg tcg                                 33

<210> SEQ ID NO 8
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 8
ggttaacggc gcctggtacc gagctccacc gcg                                 33
```

METHODS FOR TRANSFORMING PLANT PLASTIDS AND MAKING TRANSPLASTOMIC PLANTS

This application is a national stage entry under 35 U.S.C. §371 of PCT/US01/09318, filed Mar. 22, 2001, which claims priority under 119(e) of U.S. application Ser. No. 60/191,147, filed Mar. 22, 2000.

TECHNICAL FIELD

The present invention generally relates to introducing exogenous nucleic acids into plants, and more particularly to methods of transforming plastids.

BACKGROUND OF THE INVENTION

Plastids are a family of closely related organelles that in one form or another are present in all living plant cells. All plastids share certain features. For example, they have their own small genome and are enclosed by an envelope composed of a double membrane. All plastids develop from protoplastids, relatively small organelles present in meristematic cells. Plastids develop according to the requirements of each differentiated cell. For instance, if the leaf is grown in darkness, the protoplastids develop into etioplasts that contain a yellow chlorophyll precursor called protochlorophyll. If, on the other hand, the leaves are grown in light, the etioplasts further develop into chloroplasts by converting protochlorophyll to chlorophyll. Chloroplasts are the site of photosynthesis, the process by which plants manufacture their own organic nutrients. Other forms of plastids are chromoplasts that accumulate carotenoid pigments. These plastids are responsible for the yellow-orange-red coloration of petals and fruit in many species. Leucoplasts are basically enlarged proplastids. They occur in many epidermal and internal tissues that do not become green and photosynthetic. Amyloplasts are a common form of leucoplasts. They store starch in storage tissues and, in certain cells of the stems, leaves and roots function as part of the plant response to gravity. All plastids contain multiple copies of the plastid genome and most are capable of division within the cell. The only type of cell and higher plant that loses its population of plastids is the male sperm cell in certain species. Thus, plastids of plants such as *maize* are maternally inherited. That is, they acquire their plastids solely from the egg cell. See, Alberts, et al., Molecular Biology of the Cell, Garland Publishing (New York), 1983, pp. 1120–1122.

The plastid genome of higher plants is a circular double-stranded DNA molecule of 120–165 kilobases that may be present in 2,000–50,000 copies per leaf cell. The plastid genome has become a very attractive target for genetic manipulation compared to the nuclear genome of the plant for several reasons. Since proteins in plastids may be expressed at a very high level, the molecular machinery of plastid is essentially a bacterial one. Also, a higher degree of containment can be achieved (no transmission via pollen) and because integration of heterologous DNA occurs via homologous recombination mechanism. DNA integrates randomly into the nuclear genome of a plant. The location of integration in the plastid genome, on the other hand, may be controlled such as by way of specific flanking sequences. There is no gene silencing or so-called position effects, so the level of expression is much more predictable. The level of expression is also much higher because there are many more DNA copies per plant cell. The chloroplast is basically a bacterium so it accommodates bacterial nucleic acid more readily than genomic DNA, without as much need for modification. This advantage applies equally to associated regulatory sequences such as bacterial promoters. The risk of gene release into the environment (referred to as "outcrossing") is essentially eliminated because chloroplasts do not move into pollen. Lastly, since the chloroplast is the site of most important biosynthetic pathways e.g., starch, amino acids and fats, it is relatively easy to insert genes and have them function in the organelle of interest without a need for special targeting sequences.

Plastid transformation has proven extremely difficult, particularly in agronomically valuable crops. Most transformation methods are species- and variety-specific. Collectively, these limitations appear to reflect complex and uniquely species-specific ways in which transformed plastids are being selected in in vitro grown plant tissues. Only the reproducible production of transplastomic, fertile tobacco plants has been reported (Svab, et al., Proc. Natl. Acad. Sci. USA 87:8526–8530 (1990). A transplastomic *Arabidopsis* plant is reported in Sikdar, et al., Plant Cell Rep. 18:20–24 (1998) but these plants were sterile. The lack of success in this area despite the large investment being made illustrates the magnitude of the problem. Hence, there is a pressing need for methods of producing transplastomic plants.

SUMMARY OF THE INVENTION

A first aspect of the present invention is directed to a method of transforming plastids. The method entails conducting steps:

(a) transferring a plastid from a cell of a first plant to a cell of a second, genetically distinct plant;

(b) introducing nucleic acid of interest into the plastid, thus producing a transformed plastid; and (c) transferring the transformed plastid into a cell of a third plant wherein the first and third plants may be genetically identical or distinct from each other.

In preferred embodiments, the plastid transfers from one plant to another are conducted on the cellular level and involve somatic cell fusion. A protoplast derived from a cell of the first plant is fused with a protoplast derived from a cell of the second plant, thus forming a cybrid. In other preferred embodiments, the transferred plastid becomes genetically recombined with a plastid of the second plant, resulting in the formation of a recombinant plastid. The recombinant plastid is then transformed with the nucleic acid. In yet other preferred embodiments, the first and third plants are members of the same plant family or more preferably, species within the same genus. Tobacco is a preferred recipient plant (i.e., the second plant or the clipboard plant) in which transformation with the nucleic acid is carried out. *Brassica* is another preferred recipient plant.

A second and related aspect of the present invention is directed to a method of making a transplastomic plant, comprising:

(a) transferring a plastid from a cell of a first plant to a cell of a second, genetically distinct plant;

(b) introducing nucleic acid of interest that includes a selectable marker gene into the plastid, thus producing a transformed plastid;

(c) transferring the transformed plastid into a cell of a third plant wherein the first and third plants may be genetically identical or distinct from each other; and (d) regenerating a transplastomic plant from cells of (c) that express the marker gene.

The transplastomic plants, per se, and parts thereof e.g., leaves, roots, stems, shoots, and seed derived from the plant are also provided. In preferred embodiments, the plants are homoplastomic.

A third aspect of the present invention is directed to a method for transforming plastids, comprising:

(a) introducing nucleic acid of interest into a plastid of a cell of a first plant, thus producing a transformed plastid; and (b) transferring the transformed plastid to a cell of a second plant, wherein the first and second plants are genetically distinct.

In this aspect, transformation of the plastid is conducted prior to the transfer of the plastid to another plant In preferred embodiments, the first and second plants are members of the same family, and more preferably are species within the same genus. Other preferred embodiments stated above in connection the first aspect of the invention apply here.

A fourth and related aspect of the present invention is directed to a method for preparing a transplastomic plant. The method entails steps:

(a) introducing nucleic acid of interest which includes a selectable marker gene into a plastid of a cell of a first plant, thus producing a transformed plastid;

(b) transferring the transformed plastid to a cell of a second plant, wherein the first and second plants are genetically distinct; and (c) regenerating a transplastomic plant from cells of (b) that express the selectable marker gene.

A fifth aspect of the present invention is directed to a plant cell or protoplast obtained from a plant, or a culture of said cell or protoplast, comprising a plastid obtained from a genetically distinct plant, wherein the plastid is transformed with a DNA molecule of interest. In preferred embodiments, the plant cell is a *Nicotiana* cell, a *Solanum* cell, an *Orychophragmus* cell, a *Lesquerella* cell, or a *Brassica* cell. In other preferred embodiments, the plastid is obtained from potato, tomato, eggplant, *Licium*, or *Brassica*. In yet other preferred embodiments, the recipient or clipboard plant cell is a tobacco cell and the plastid is obtained (or "donated") from another member of the Solanaceae family e.g., potato, tomato, eggplant and *Licium barbarum* L. In other preferred embodiments, the recipient plant cell is an *Orychophragmus* cell or a *Lesquerella* cell and the plastid is obtained from *Brassica napus* L. In other embodiments, the recipient and donor plants are members of the Gramineae family.

The methods of the present invention are particularly advantageous because they provide for relatively easy and efficient plastid manipulation in essentially all crop species, particularly economically important varieties.

BEST MODE OF CARRYING OUT THE INVENTION

Figure 1:
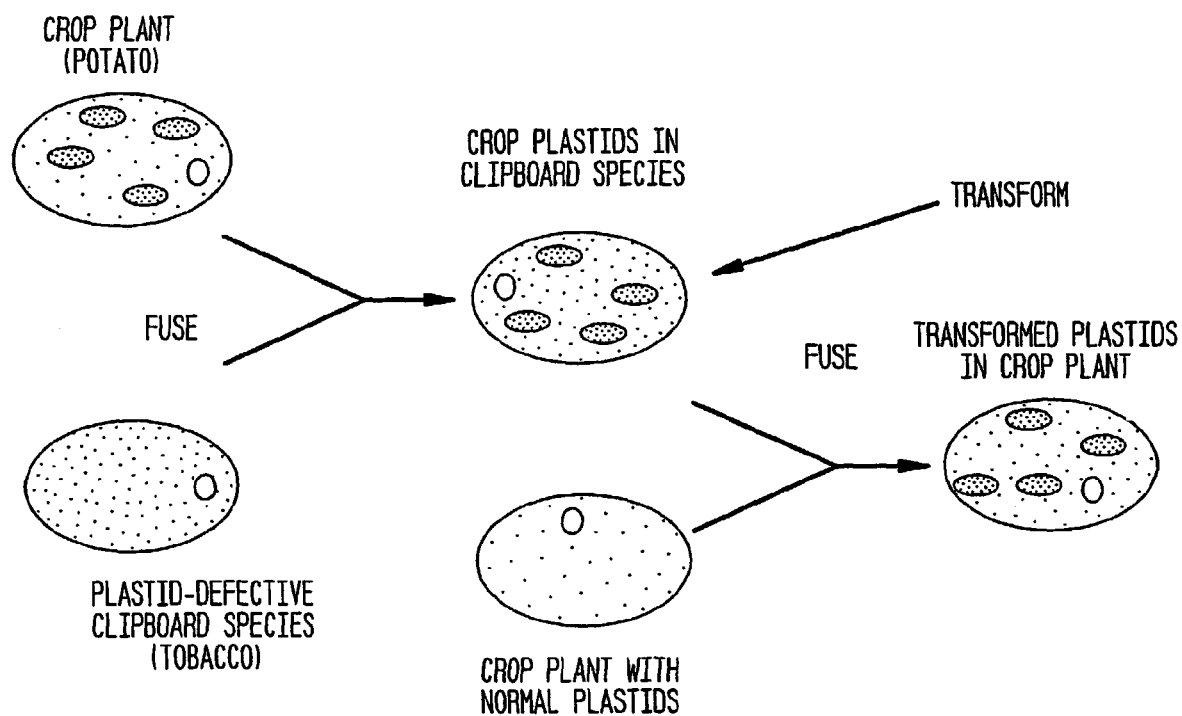
FIG. 1 is a schematic illustration of an embodiment of the present invention.

The difficulty in preparing transplastomic plants is not only related to introducing the exogenous nucleic acid at the cellular level. Rather, a particularly troublesome aspect of the overall challenge has been the lack of regenerability of the transplastomic cells, particularly to the extent that homoplastomic cells are produced. See, Bilang, et al., Nature Biotech. 16:333–334 (1998). By the term "homoplastomic", it is meant cells containing no wild-type plastome (i.e., plastid genome) in their plastids. That is, all plastids contain the nucleic acid of interest. Besides the poor regenerability, the selection of homoplastomic plant cells is extremely difficult.

The present invention circumvents both of these major obstacles by moving or relocating the plastids that are to be transformed into a nuclear environment in which selection of homoplastomic cells is readily accomplished. The recipient cell provides a compatible and hospitable environment for the plastid and the transformation of the exogenous nucleic acid into the plastid. Following transformation, the recipient or clipboard cell continues to grow and divide in the more easily transformed nuclear background facilitating the selection of homoplastomic cells.

According to one aspect of the present invention, a process of transformation of plant plastids is provided wherein nucleic acid of interest is introduced into a plastid in a non-native environment. The transformed plastids are moved back into cells of the original plant or a genetically distinct plant. "Genetically distinct" plants as the term is used herein, are meant to include mutants of the same species, different species, genuses and families. The term "plant" is meant to include all higher plants, preferably flowering plants. Similarly, individual plants e.g., "potato"

and "tomato" as used herein, are meant to include all forms, lines and varieties of potato and tomato, etc. "Transformed" is used herein to mean genetically modified by the incorporation of nucleic acid of interest (e.g., encoding a protein) into plant plastids. In general, the nucleic acid is DNA exogenous to the donor plant (i.e., the plant from which the plastid originates), the recipient and/or the ultimate recipient. By "exogenous", it is meant that the nucleic acid is not normally found in the plant that is to be transformed or not normally found at the copy number that is being introduced. In preferred embodiments, the nucleic acid is exogenous to the donor plant.

Tobacco is a preferred recipient (or clipboard) for the plastids of interest. A series of remote cybrids were designed that combine a tobacco nucleus, on one hand, and plastids of other economically significant *Solanaceae* species (potato, tomato, pepper, nightshade, thorn apple), on the other. Those cybrids were then tested for plastid transformability, and the resultant transformed plastids were then returned to their original nuclear background, thus giving rise to transplastomic plants. The same approach has been applied to a crucifer plant family, thus illustrating broad applicability of the invention. In general, plant pairs that may be used in the methods of the present invention can be selected using the following protocol. A candidate for the recipient (or "clipboard") plant is mutated. Mutants containing plastids that do not synthesize chlorophyll ("white mutants") are selected. Protoplasts derived from the candidate plastid donor are treated e.g., irradiated, to kill the nuclei. Protoplasts derived from the white mutants are fused with the treated protoplasts derived from the candidate donor. Green colonies and regenerating cybrids or somatic hybrids are selected. The green colonies contain functional plastids transferred from the donor. The irradiation ensures that the only possible transformation event involves a plastid and not a nucleus. The formation of green colonies demonstrates that the donor and recipient plants are compatible, at least insofar as the plastids are concerned.

Transfer of plastids from one plant species to another may be carried out most easily by fusing protoplasts derived from the donor and recipient cells, and then from the recipient to the ultimate plant Recombination of plastids is a random event but such events can be identified using standard techniques in molecular biology. Plastid transfer can be accomplished by sexual hybridization wherein pollen provides the non-native nuclear environment.

The preferred method for the introduction of the nucleic acid of interest is by particle gun (biolistics) or PEG-mediated gene transfer. See, Daniell Methods Enzymol. 217:536–556 (1993); Ye, et al., Plant Mol. Biol. 15:809–819 (1990); Daniell et al., Proc. Natl. Acad. Sci. U.S.A. 87:88–92 (1990); Daniell, et al., Plant Cell Reports 9:615–619 (1991) and Svab, et al., Proc. Natl. Acad. Sci. U.S.A. 90:913–917 (1993). The nucleic acid includes a marker in order for the identification of transformants. Selection schemes include spectinomycin resistance due to a mutation in plastid 16S ribosomal RNA genes or conferred by the expression of an engineered bacterial aadA (Svab, et al., Proc. Natl. Acad. Sci. USA 87:8526–8530 (1990); Svab & Maliga, Proc. Natl. Acad. Sci. USA 90:913–917 (1993)) and resistance to kanamycin based on expression of neomycin phosphotransferase (Carrer, et al., Mol. Gen. Genet. 241:49–56 (1993)). The marker gene does not have to be physically linked to the DNA e.g., encoding the protein of interest; it may be delivered via another vector. See, Carrer, et al., BIO/TECHNOLOGY 13:791–794 (1995). It is preferred but not essential that the nucleic acid is integrated into the plastid genome. To facilitate efficient and targeted integration of the nucleic acid of interest into the plastid genome, the nucleic acid is flanked by DNA sequences present in the target plastid. Specific sequences are exemplified in the examples. See also International Patent Publications WO 00/28014 ("Plastid Transformation of Solanaceous Plants") and WO 00/39313 ("Plastid Transformation of *Brassica*").

The nucleic acid of interest varies widely and embraces any DNA encoding proteins whose expression in plants would be valuable from some standpoint. The invention is particularly suited to the manifestation of new traits in the transplastomic plant that require very high levels of expression. The transplastomic plants produced in accordance with the present invention contain thousands of copies of the DNA in each cell, leading to extraordinary levels of gene expression. The DNAs and proteins fall into the broad categories of crop protection, crop improvement, production of specialty compounds including specific chemicals, neutraceuticals and other products associated with food quality such as modified starch, oils and protein compositions, that, in total, require the expression of a coordinate set of genes and thus a specialized transformation system in order to have the plant exhibit the trait of interest. The exogenous genes can be useful for modifying the input requirements of a plant such as their response to the environment, their ability to protect themselves from pests, protection from xenobiotic agents, or which alter other traits such as overall yield, production of nutritionally balanced protein, better quality starch, high quality or quantity of oil or vitamin levels. The genes may also allow the plants to perform functions they normally do not perform such as the production of pharmaceuticals such as proteins (e.g., growth hormones such as somatotropins), antigens and small molecules. For example, the literature has reported the genetic engineering of plastids with transgenes that impart resistance to insects and herbicides and cytoplasmic male sterility. See, McBride, et al., Bio/Technology 13:362–365 (1995) (transplastomic tobacco leaves containing "unprecedented" 3–5% of cryIAC protein); Kota, et al., Proc. Natl. Acad. Sci. USA 96:1840–1845 (1999) (reporting over expression of Bt Cry2Aa2 protein in chloroplasts to reduce insect resistance); McBride & Maliga, PCT patent, WO 95/24492; McBride & Stalker, PCT patent WO 95/24493; Daniell, et al., Nature/Biotechnology 16:345–348 (1998); Blowers, et al., PCT patent WO 99/05265; Maliga, PCT patent WO 95/25787.

An embodiment of the invention is schematically illustrated in FIG. 1. Initially a host (clipboard) can be produced that is white due to impaired chloroplast function. The clipboard is chosen that is easy to transform and regenerate. The chloroplasts from the species of interest are transferred to the clipboard plant by protoplast fusion and a stable intermediate is produced. Plants regenerated from this fusion product that contain the nucleus of the clipboard species and the plastids of the target species are normal and stable. Transformation is performed in these cybrids. Fusion from the cybrids to the target species can be performed using protoplasts derived from a homoplastidic cybrid plant thereby producing the target plant with transformed plastids. Whole plants may be regenerated from these cells.

In another aspect of the invention, the plastids are transformed in their native environment and then transformed into a genetically distinct plant. This method is particularly advantageous when the donor plant can provide plastids to a number of related recipient plants (e.g., members of the Solanaceous family). Cells (or protoplasts) containing the transformed plastid, wherein the plastid is native to a genetically distinct plant, and cultures of the cells or protoplasts, may be isolated or prepared in accordance with standard techniques.

Once the transformed plastids have been transferred into or formed within the cells of the ultimate recipient plant, transplastomic plants are regenerated from cells that express the selectable marker gene. In preferred embodiments, the plants are regenerated from homoplastomic cells. Homoplastomy may be achieved in accordance with standard techniques such as selective elimination of wild-type plastome copies during repeated cell divisions on a selective medium. Copy number of the DNA (i.e., the introduced sequences) is indicative of whether homoplastomy has been achieved. See, Daniell, et al., (1998), supra, Kanevsld, et al., Plant Physiol. 119:133–141 (1999) (obtaining homoplastomic spectinomycin resistant plants by a repeated cycle of shoot regeneration from leaves on the same selective medium and then rooting the shoots on antibiotic-free Murashige-Skoog agar). Once homoplastomic recipient cells are obtained, the transformed plastids are transferred to a cell of the donor plant. The homoplastomic nature of the recipient facilitates the selection following transfer. Preferably, the transfer is conducted via fusing protoplasts derived from the respective cells. Fertile plants may be regenerated from the protoplasts in accordance with standard techniques. Obtaining various plant parts such as roots, shoots, leaves and stems, and deriving seed from the plants are likewise accomplished using standard procedures.

The transplastomic plants of the present invention are believed to possess traceable genetic differences that distinguishes them on a genetic level from plants generated through direct plastid transformation. The most noticeable distinctions concern mitochondrial DNA composition of the material in question (GLEBA, Y. Y., SYINIK, K. M. (1984) Protoplast Fusion. Springer, Berlin, Heidelberg, New York, 1–220). Mitochondrial DNA of higher plants is polymorphic and any interspecific cell hybridization invariably generates clearly unique rearrangements that, for the most part, have no phenotypic effect (GLEBA, Y. Y., SHLUMUKOV, L. R. (1990) Somatic hybridization and cybridization. In: Bhojwani, S. S. (ed.) Plant Tissue Culture: Applications and Limitations. Elsevier, Amsterdam, Oxford, New York, 316–344). Yet they can easily be recognized through a standard molecular biology method of mitochondrial DNA analysis, such as restriction profiling or polymerase chain reaction, etc., of the parental species versus the material generated in the first and second rounds of cell hybridization. Thus, the material resulting from "clipboard"-mediated plastid transformation is genetically unique and in this regard, different from transplastomic materials obtained using alternative technologies.

In addition to the mitochondrial composition, the plants regenerated from cells containing transformed plastids that are not native to the plant are completely distinguished from transplastomic crop plants produced by direct approach. For example, the methods of the present invention produce completely functional potato (*Solanum tuberosum*) containing transformed chloroplasts from *Solanum rickii*, *Solanum cardiophyllum*, or *Solanum papita*. Functional cybrids of potato with those plastomes were also described Sidorov, Samoylov, Samoylov, Glagotskaya, Gleba, Proc Academy of Sci USSR, 308, 741–744(1989) and Sidorov, Yevtushenko, Shakhovsky, and Gleba, Theor. Appl. Genet. 88:525–529 (1994).

In preferred embodiments, the plant cell is a *Nicotiana* cell, a *Solanum* cell, an *Orychophragmus* cell, a *Lesquerella* cell, or a *Brassica* cell. In other preferred embodiments, the plastid is obtained from potato, tomato, eggplant, *Licium*, or *Brassica*. In yet other preferred embodiments, the recipient or clipboard plant cell is a tobacco cell and the plastid is obtained (or "donated") from another member of the Solanaceae family e.g., potato, tomato, eggplant and *Licium barbarum* L. In other preferred embodiments, the recipient plant cell is an *Orychophragmus* cell or a *Lesquerella* cell and the plastid is obtained from *Brassica napus* L. In other embodiments, the recipient and donor plants are members of the Gramineae family.

The state of the art with respect to plastid transformation, including techniques and genetic elements useful therein, are described in one or more of the following publications.

Daniell & McFadden, U.S. Pat. No. 5,693,507;
McBride & Maliga, U.S. Pat. No. 5,545,818;
McBride & Maliga, PCT patent, WO 95/24492;
McBride & Stalker, PCT publication WO 95/24493;
McBride & Stalker, PCT publication WO 95/16783;
Maliga, PCT publication WO 95/25787;
Maliga, Allison, and Haydukiewicz, PCT publication WO 97/06250;
Maliga, Carrer, and Chaudhuri, PCT publication WO 97/47771;
Maliga & Maliga, U.S. Pat. No. 5,451,513;
Maliga, Sikdar, and Reddy, PCT publication WO97/32977
Baldev, Gaikwad, Kirti, Mohapatra, Prakash, and Chopra, *Mol. Gen. Genet*, 260: 357–361 (1998);
Boynton, Gillham, Harris, Hosler, Johnson, Jones, Randolph-Anderson, Robertson, Klein, Shark, and Sanford, *Science,* 240:1534–1537 (1988);
Carrer, Hockenberry, Svab, and Maliga, Molec. Gen. Genet. 241:49–56 (1993);
Daniell, Datta, Gray, Varma, and Lee, *Bio/Technology* 16:345–348 (1998);
Eigel & Koop, *Mol. Gen. Genet.* 233:479–482 (1992);
Fahleson, Eriksson, Landgren, Stymne, and Glimelius, *Theor. Appl. Genet.* 87: 795–804 (1994)
Gleba & Sytnik, *Monogr. Theor. Appl. Genet,* 8:1–220 (12984);
Jarvis, Chen, Li, Peto, Fabkhauser, and Chory, *Science* 282:100–103 (1998);
Kermickle, *Science* 166:1422–1424 (1969);
Kindiger, *Crop Sci,* 34:321–322 (1994);
Koop, Steimueller, Wagner, Roessler, Eibl, Sacher, *Planta* 199:193–201 (1996);
Kota, Daniell, Varma, Garczynski, Gould, and Moar, *Proc. Natl. Acad. Sci. USA* 96:1840–1845 (1999);
Kushnir, Shlumukov, Pogrebnyak, Berger, and Gleba, *Mol. Gen. Genet,* 209:159–163 (1987);
McBride, Svab, Schaaf, Hogan, Stalker, and Maliga, *Bio/Technology* 13:362–365 (1995);
Ramulu, Dijkhuis, Famelaer, Cardi, and Verhoeven, *Planta* 190:190–198 (1993);
Sidorov, Yevtushenko, Shakhovsky, and Gleba, *Theor. Appl. Genet.* 88:525–529 (1994);
Sidorov, Kasten, Pang, Hajdukiewicz, Staub, Nehra, *The Plant J.* 19:209–216 (1999);
Sikdar, Serino, Chaudhuri, and Maliga, *Plant Cell Rep,* 18:20–24 (1998);
Strepp, Scholz, Kruse, Speth, and Reski, *Proc. Natl. Acad Sci. USA* 95:4368–4373 (1998);
Svab, Hajdukiewicz, and Maliga, *Proc. Natl. Acad. Sci. USA* 87:8526–8530 (1990);
Svab and Maliga, *Proc. Natl. Acad Sci. USA* 90:913–917 (1993);
Thanh & Medgyesy, *Plant Mol. Biol,* 12:87–93 (1989);

Thanh, Smith, Medgyesy, and Marton, *Mol. Gen. Genet.* 213:186–190 (1988);

Verhoeven, van Eck, Blaas, and Dijkhuis, *Plant Cell Rep.* 14:781–785 (1995);

Wolters, Vergunst, van der Werff, and Koomeef, *Mol. Gen. Genet*, 241:707–718 (1993).

Zubko & Day, *Plant J.* 15:265–271 (1998);

Zubko, Zubko, Patskovsky, Khvedynych, Fisahn, Gleba, and Schieder, *J. Exp. Botany* 47:1101–1110 (1996).

The experiments described below provide examples of successful plastid transformation for significant crop species (potato, tomato, pepper, thorn apple, nightshade, and crucifers) based on use of systems with a nuclear background that favor plastid transformation.

EXAMPLE I

Transformation of *Salpiglossis* Plastids and Production of *Salpiglossis* transplastomic plants

Figure 2:
FIG. 2 is a photograph of an ethidium bromide-stained gel showing the presence of exogenous DNA in various plants. PCR amplification reaction was performed with primers specific to the internal part of the aadA gene. Amplified product is 479 bp. As positive control the DNA of transformed *N. tabacum* was used. Lane 1—Potacco (i.e., a potato/tobacco recombinant plastid), nontransformed plant (negative control); 2—Potacco, clone 1; 3—Potato, clone 2; 4—Potacco, clone 3; 5—*N. tabacum*, transformed plant (positive control), 478 bp; 6—*N.t.(Atropa)* cybrid; 7—*N.t. (Scopolia)* cybrid; 8—*N.t.(Salpiglossis)* cybrid; 9—1 kb DNA Ladder.
Figure 3:
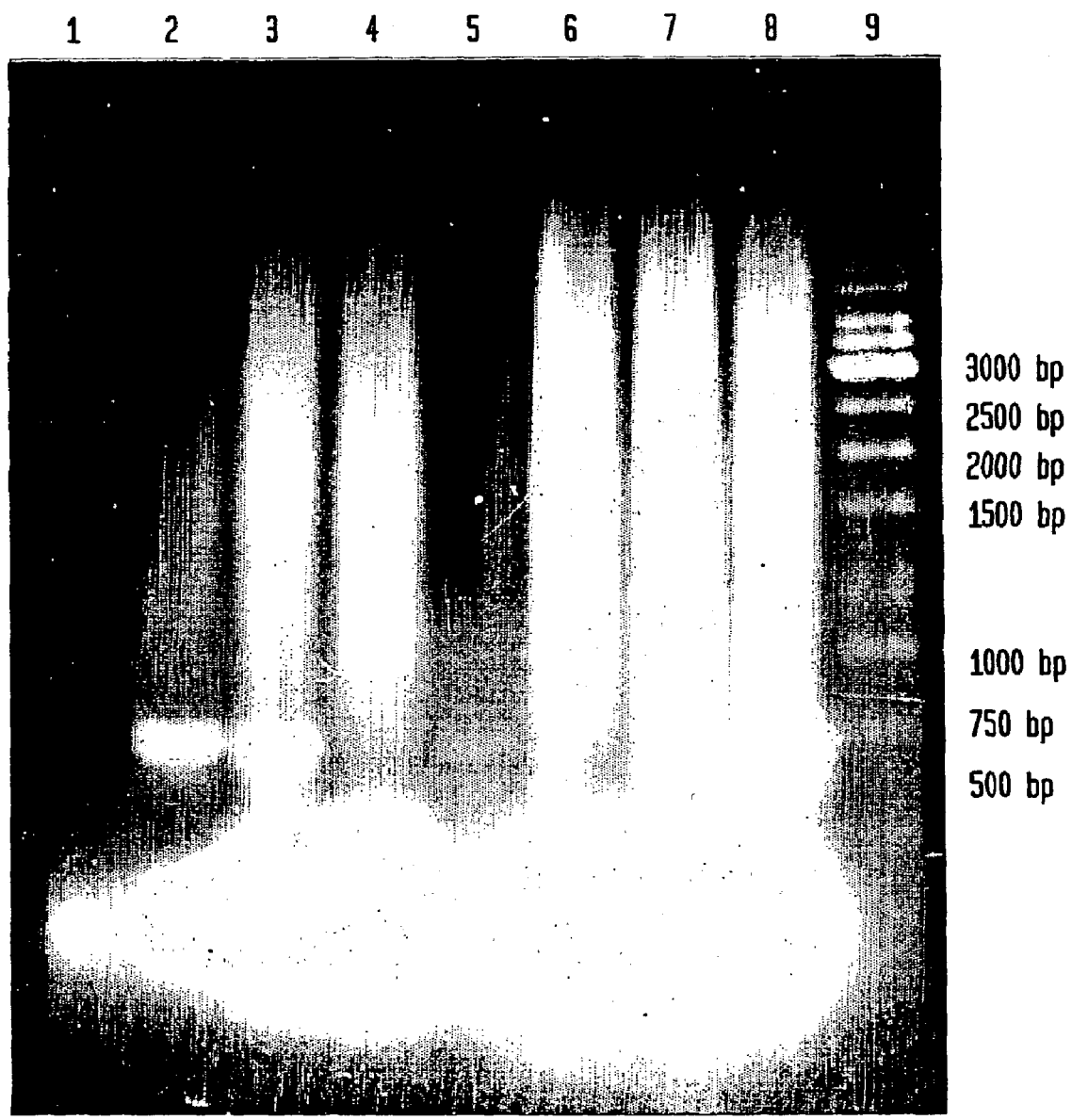
FIG. 3 is a photograph of an ethidium bromide-stained gel indicating the presence of exogenous DNA in plants. PCR amplification reaction was performed in which one primer was specific to the internal part of the aadA gene and the other primer was specific for chloroplast genomic DNA. The size of the amplification product is between 1100–1400 bp. As positive control the DNA of transformed *N. tabacum* was used. Lane 1—1 kb DNA Ladder; 2—*N. tabacum*, transformed plant (positive control); 3—Potacco, clone 1; 4—Potacco, clone 2; 5—*N.t.(Salpiglossis)* cybrid.

*Salpiglossis sinuata* L., plants and tobacco mutant plants with a plastome-encoded chlorophyll deficiency (Kushnir, et al., Mol. Gen. Genet 209:159–163 (1987)) were grown in vitro as described in Sidorov, et al., Theor. Appl. Genet. 88:525–529 (1994). Mesophyll protoplasts were isolated and fused according to the standard protocol described in Gleba & Sytnik, Monogr. Theor. Appl. Genet. 8:1–220 (1984). Green recombinants were regenerated and green tobacco-looking plantlets selected. Several independent photosynthesizing lines were selected and further analyzed. Recombinants combining *Salpiglossis* plastids and tobacco nuclei were subjected to plastid transformation using published protocols (Koop, Steinmueller, Wagner, Roessler, Eibl, Sacher, Planta 199:193–201 (1996) based on PEG-mediated gene delivery combined with selection on spectinomycin and streptomycin (Svab, et al., Proc. Natl. Acad. Sci. USA 87:8526–8530 (1990)). Several independent putative transformants were selected and further tested. Among the plant material produced, truly stable plastid transformants were identified. See FIGS. 2 and 3. Mesophyll protoplasts from these plants were then isolated and fused with somatic cells from *Salpiglossis* line. No albino mutants were needed, because the str/spm resistant chloroplasts were readily identified. A number of photosynthesizing spectinomycin/streptomycin resistant regenerants were obtained that are *Salpiglossis*-looking plants containing transplastomic *Salpiglossis* plastids (photo not shown).

EXAMPLE II

Transformation of Tomato Plastids

In these experiments, in vitro grown normal plants of tomato, *Lycopersicon esculentum* L., and kanamycin and hygromycin resistant plants of *Solanum nigrum* were used The culture conditions and fusion protocols used were essentially as described in Wolters, et al., Mol. Gen. Genet. 241:707–718 (1993). The clipboard lines were produced by fusion between *Lycopersicon esculentum* L. and irradiated *Solanum nigrum*. The produced plant had flowers, but were male sterile. The green regenerants that were produced contained *Lycopersicon* chloroplasts and hybrid nuclear material from both parents initially. Transformation and putative transplastomic selection were as described in Example I. Stable transplastomic plants were pollinated with normal tomato plant. Seeds were obtained and tomato-like plants with transformed plastids were grown.

EXAMPLE III

Transformation of *Solanum melongena* Plastids

*Solanum melongena* plants and tobacco mutant plants with a plastome-encoded chlorophyll deficiency (Kushnir, et al., Mol. Gen. Genet. 209:159–163 (1987)) were grown in vitro as described in Sidorov, et al., Theor. Appl. Genet. 88:525–529 (1994). Mesophyll protoplasts were isolated and fused according to the standard protocol of Gleba & Sytnik, *Monogr. Theor. Appl. Genet.*, 8, 1–220, (1984). Green recombinants were regenerated and green plantlets were selected that looked like tobacco. Several lines were isolated and selected for further analysis. Recombinants that contained *Solanum* plastids and tobacco nuclei were treated using the protocol described in Koop, et al., Planta 199: 193–201 (1996) using PEG-mediated gene delivery combined with selection on spectinomycin and streptomycin (Svab, et al., Proc. Natl. Acad. Sci. USA 87:8526–8530 (1990)) to obtain transformed plastids. Several independent putative transformants were selected and further tested. Stable plastid transformants were identified from the plant material as demonstrated in FIGS. 2 and 3. Mesophyll protoplasts from these plants were then isolated and fused with somatic cells from *Solanum* line. Since the chloroplasts were str/spm resistant, the albino mutants were not needed. A number of photosynthesizing spectinomycin/streptomycin resistant regenerants obtained were *Solanum*-looking plants containing transplastomic *Solanum* plastids (photo not shown).

EXAMPLE IV

Transformation of *Atropa* Plastids and Production of *Atropa* Transplastomic Plants In vitro grown normal plants of nightshade, *Atropa belladonna* L., were grown instead of *Salpiglossis*. The tobacco mutant plants with a plastome-encoded chlorophyll deficiency were again used as recipient in these experiments. All other conditions and experiments were essentially as described in Example I. Following fusion of the Atropa protoplasts with tobacco, transformation and fusion to move the transformed plastids from tobacco back into *Atropa* green plants were obtained that looked like *Atropa*.

EXAMPLE V

Transformation of *Licium* Plastids and Production of *Licium* Transplastomic Plants In vitro grown normal plants of *Licium barbarum* L. instead of *Salpiglossis* and tobacco mutant plants with a plastome-encoded chlorophyll deficiency as recipient were used in this experiment. All other conditions and experiments were as described in Example I.

EXAMPLE VI

Transformation of Potato, *Solanum tuberosum* L. Plastids.

In vitro grown normal and albino plants of *Solanum tuberosum* L. instead of *Salpiglossis* were used in this experiment. As a recipient species, a wild *Solanum* species, *Solanum rickii* L., was used. For culturing mesophyll protoplasts of in vitro grown plants of *S. rickii*, an enriched culture medium was used that included vitamins and amino acids as described in Thanh, et al., Plant Mol. Biol. 12:87–93

(1989). All other conditions and experiments were essentially as described in Example I.

EXAMPLE VII

Transformation of *Brassica napus* Plastids

Canola, *Brassica napus* L., normal plants and *Orychophragmus* or *Lesquerella* mutant plants with a plastome-encoded chlorophyll deficiency were grown in vitro as described (Zubko, et al., (1998), supra). Mesophyll or coleoptile protoplasts were isolated and fused according to the standard protocol (Fahleson, et al., Theor. Appl. Genet 87:795–804 (1994). Green recombinants have been regenerated and green *Orychophragmus*- and *Lesquerella*-looking plantlets selected Several independent photosynthesizing lines were selected and further analyzed. Recombinants combining canola plastids and *Orychophragmus* or *Lesquerella* nuclei were subject to plastid transformation using published protocols based on particle gun-based gene delivery combined with selection on spectinomycin and streptomycin. Several independent putative transformants were selected and tested further. Among the material produced true stable plastid transformants were identified. Mesophyll protoplasts from these plants were then isolated and fused with a somatic cells from canola line. A number of photosynthesizing str/spm resistant regenerants obtained were canola-looking plants containing transplastomic canola plastids.

EXAMPLE VIII

Transformation of Recombinant *Nicotiana+Solanum* Plastids

Figure 4:
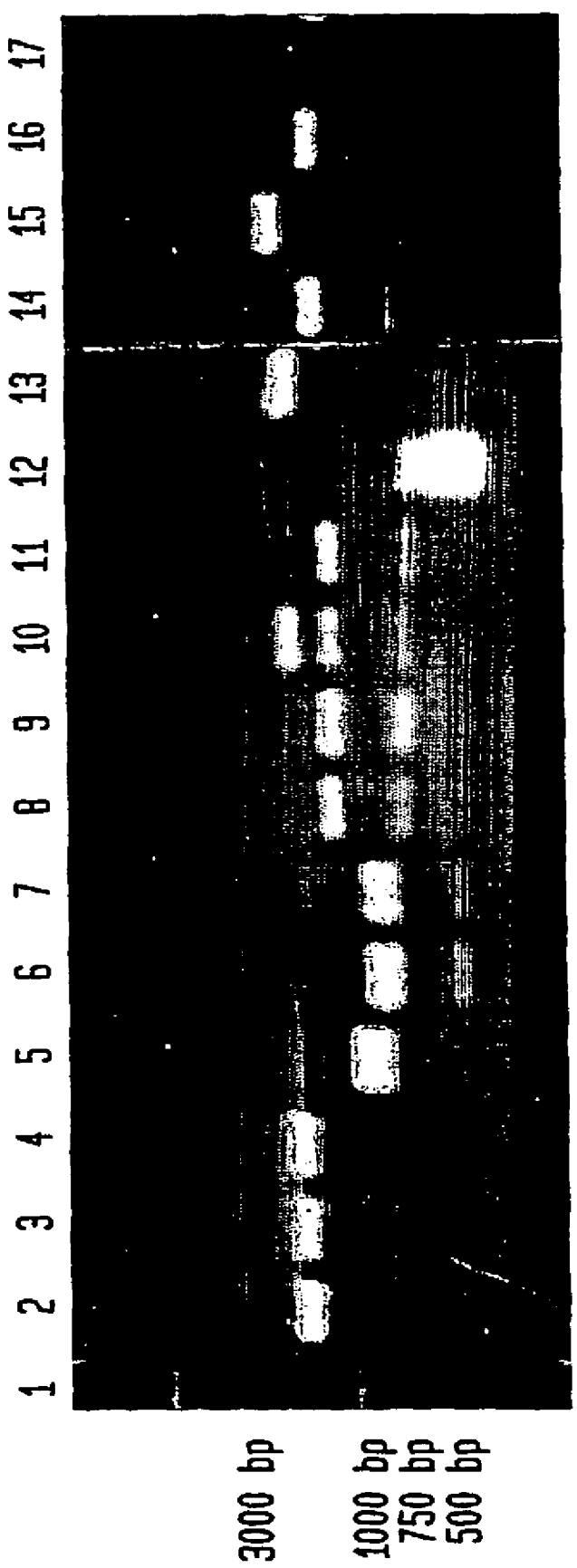
FIG. 4 is a photograph of an ethidium bromide-stained gel showing the chimeric nature of the plastids in the potato/tobacco recombinant plastid. Chloroplast genomes of tobacco (Lanes 2, 5, 8, 11, 14), potato (Lanes 3, 6, 9, 12, 15) and potato (Lanes 4, 6, 10, 13, 16) were compared. The fragment trnL-ndhD was undigested (Lanes 2–4) or treated with Dra I (Lanes 5–7), StyI (Lanes 8–10), EcoRI (Lanes 11–13) or HaeIII (Lanes 14–16) restriction endonucleases.

In vitro grown normal and albino plants of *Solanum tuberosum* L., were used in this experiment. Recombinant plants combining tobacco nucleus and recombined tobacco-potato plastome (FIG. 4) were produced essentially as described in Thanh, et al., Plant Mol. Biol. 12:87–93 (1989). All other conditions and experiments were essentially as described in Example I. Normal potato plants were produced that contain recombinant and transplastomic plastids expressing antibiotic resistance. See FIGS. 1 and 2.

EXAMPLE IX

Construction of Plastid Transformation Vector pCB033

A 4656 bp Bgl II fragment was excised from the tobacco (*N. tabacum*) ptDNA subclone pNtcPsl (pNtcPsl contains a tobacco plastome fragment between position 99983 and 123672; Shinozaki et al., EMBO J. 5:2043–2049 (1986)). The Bgl II fragment containing the genes ndhF, rpl32 (CDS79) and trnL (trn30) was agarose gel purified and subcloned into the Bam HI site of plasmid pBluescript KS (Stratagene, Heidelberg, Germany) yielding subclone pF4656BB.

A cassette consisting of the aminoglycoside 3'-adenyltransferase (aadA) from *E. coli* under the control of the tobacco 16S rrn promoter (16S-rDNA promoter) was cloned as follows: using the polymerase chain reaction a DNA fragment containing the rrn promoter was amplified from tobacco total DNA with the primers "5–24" 5'-CCGAATTCGCCGTCGTTCAATGAG-3' (SEQ ID NO: 1) and "3–21" 5'-CACGATATCGCCCGGAGTTG-3' (SEQ ID NO: 21). The amplified fragment was cut with both Eco RI and Eco RV. A linker DNA fragment encompassing the ribosomal binding site (RBS) of the tobacco rbcL gene was constructed by annealing primer "5-rbs" 5'-CTCGATAT-CACTAGTTGTAGGGAGGGA-3' (SEQ ID NO: 3) and primer "3-rbs" 5'-GTGCCATGGATCCCTCCT-3' (SEQ ID NO: 4). The Klenow fragment of DNA polymerase was used to fill the overhangs. Subsequently the fragment was cut with Eco RV and Nco I. The plasmid pUC-atpX-AAD (provided by Dr. M. Goldschmidt-Clermont) containing the bacterial aadA gene fused to a 440 bp fragment of the Chlamydomonas reinhardtii rbcL downstream region was cut with Eco RV and Nco I thus removing the original pUC-atpX-AAD promotor fragment. The Eco RV and Nco I treated annealing product of "5-rbs" and "3-rbs" (ribosome binding site) and the Eco RI and Eco RV treated PCR product (rrn promotor) were inserted into the promotorless pUC-atpX-AAD vector simultaneously yielding the clone pUC16SaadA.

A 1.4 kbp fragment containing the aadA expression cassette was excised from pUC16SaadA by cutting with Sma I and Eco RI. The Eco RI ends were converted into blunt ends by a fill up reaction with the Klenow fragment of DNA polymerase. The resulting blunt end fragment was the gel purified.

Vector pF4656BB was linearized using the Sna BI restriction enzyme. The linear fragment was treated with alkaline phosphatase to prevent self-circularization in the following ligation reaction. The aadA expression cassette excised from pUC16SaadA was then used in a ligation reaction with the linear fragment of pF4656BB. The resulting clones were screened for the presence of the aadA cassette. Molecules having the aadA cassette in the same orientation as the ndbF gene were selected resulting in the transformation vector pFaadA I.

A Hinc II restriction site in the multiple cloning site of the vector was removed by subcloning the Sal I/Xba I fragment (carrying the insert with the plastome sequences and the aadA expression cassette) into a pKS-minus vector, which has been linearized with Xho I/Xba I.

Figure 5:
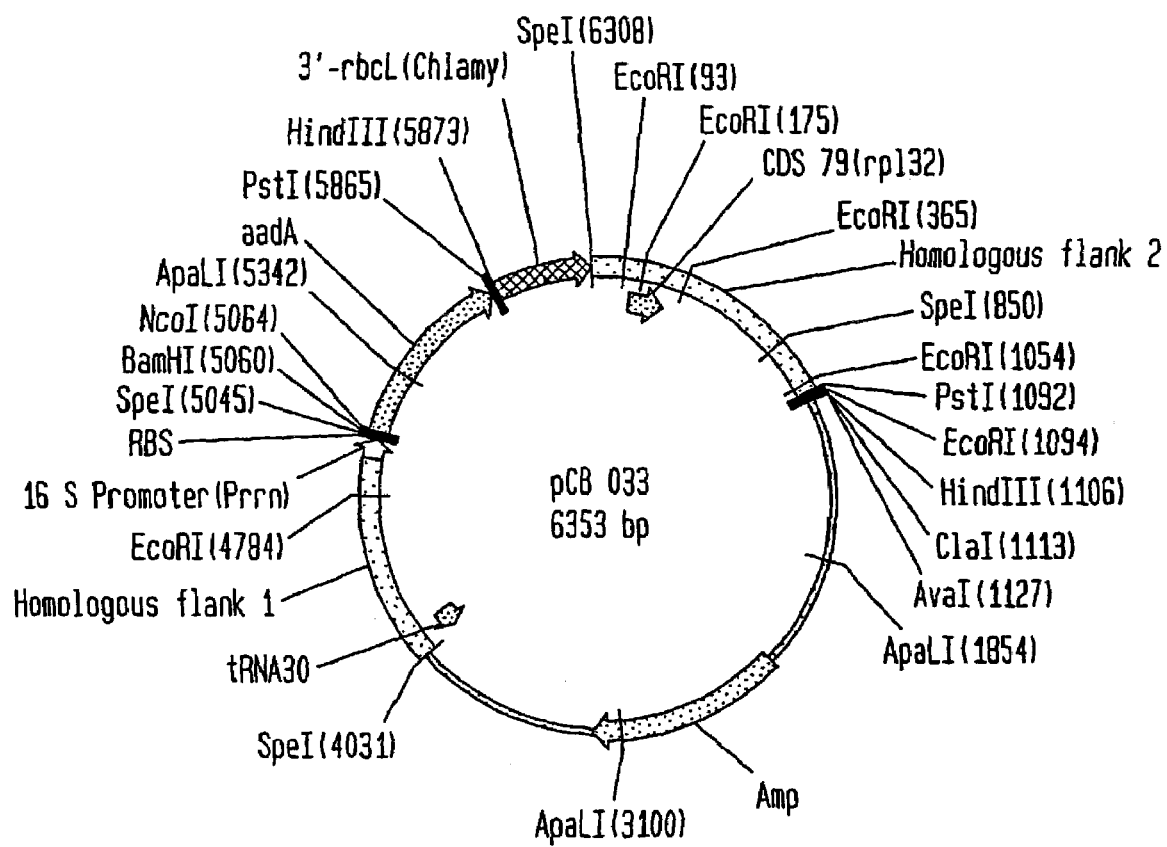
FIG. 5 is a map of plasmid pCB033 that in a preferred embodiment, is used to prepare transplastomic plants with *Solanum*-related plastids containing the aadA gene for selection on spectinomycin/streptomycin under control of the 16S rRNA promoter and flanked by sequences for integration by homologous recombination.

To reduce the overall size of the vector, the molecule was digested with Nde I and Sma I and religated after treating it with the Klenow fragment of DNA polymerase yielding plasmid pCB 033, schematically illustrated in FIG. 5.

EXAMPLE X

Construction of Plastid Transformation Vector pCB 040

Total DNA of canola (*Brassica napus*) has been isolated using the DNeasy Plant Mini Kit (QIAGEN, Hilden, Germany).

A tobacco (*N. tabacum*) plastome fragment of 2515 bp (position 140126 bp–142640 bp in tobacco plastome map) has been selected as highly conserved. Primers for PCR have been designed using this tobacco sequence:

```
Left primer:
"trn V-li-65"   5'- CCA CGT CAA GGT GAC ACT C-3'

Right primer:
"rps 7-re-66"   CTG CAG TAC CTC GAC GTG
```

PCR amplification with Pfu-Polymerase (Promega) using total DNA of Canola as a template was performed with primers "tm V-li-65" and "rps 7-re-66". After optimal conditions for PCR were determined (addition of 4 mM $MgCl_2$, annealing temperature was increased up to 57° C.) the reaction yielded a product of approximately 2800 bp, which was then agarose gel purified.

"A-tailing" enabling direct cloning of the fragment into a pGem-Tsy vector has been done using Taq DNA Polymerase (QIAGEN) as described in the pGEM-T-easy manual (Promega). The reaction was purified using the QIAquick PCR Purification Kit (QIAGEN) and used in a ligation reaction together with the pGEM-T-easy vector according to the protocol of the manufacturer. The product of the ligation was purified with the QIAquick PCR Purification Kit (QIAGEN) and used for electroporation-mediated transformation of "Epicurian Coli Sure" electrocompetent cells (Stratagene). Electroporation has been performed under standard conditions for bacteria electroporation (Capacity 25 µF, Shunt 201 OHM, Pulse 5 msec) using a Peqlab (Erlangen, Germany) electropulse device. The bacteria were spread onto ampicillin (75 mg/L) LB-agar plates containing 100 µl of 10 mM IPTG and 100 µl of 2%-X-gal.

Using a blue-white selection system, white colonies were selected and their plasmid-DNA was been isolated with the QIAprep Spin Mini Prep Kit (Quiagen).

Using restriction analysis (restriction with NotI) positive clones have been selected yielding plasmid pCan01. The plasmid DNA of positive clones was subjected to sequencing (TopLab, Martinsried, Germany). The sequence data has been used to determine the orientation of the insert and to find a suitable integration site for aadA cassette. The Bpu1102I site at position 828 was chosen as an insertion site for the aadA marker cassette.

The DNA-fragment carrying the aadA marker cassette was prepared as follows: PCR with Pfu DNA Polymerase was performed to amplify the aadA-expression cassette from the template pUC 16SaadA (see Example IX) Primers "aadA-uni-li-94" 5'-GCT CGA GAT ACC GGT CCC GGG AAT TCG CCG TCG-3' (SEQ ID NO: 7) and "aadA-uni-re-95" 5'-GGT TAA CGG CGC CTG GTA CCG AGC TCC ACC GCG-3' (SEQ ID NO: 8) were used for the PCR reaction. The PCR reaction product was purified via agarose gel electrophoresis.

The vector pCan01 was digested with Bpu1102I and the Klenow fragment has been used to generate blunt ends. Then dephosphorylation (first with Shrimp Alkaline Phosphatase followed by another treatment with calf intestine phosphatase) was carried out to prevent self-ligation. The phosphatase enzymes were inactivated by phenol extraction.

The linearized pCab01 fragment was used for a ligation reaction together with the aadA-marker fragment described above. The ligation was performed using the "Rapid Ligation Kit" (Roche, Penuberg, Germany). The ligation product was purified with the QIAquick PCR Purification Kit (QIAGEN). *Epicurian Coli* Sure electrocompetent cells (Stratagene) were transformed by the electroporation method under standard conditions as described above.

Figure 6:
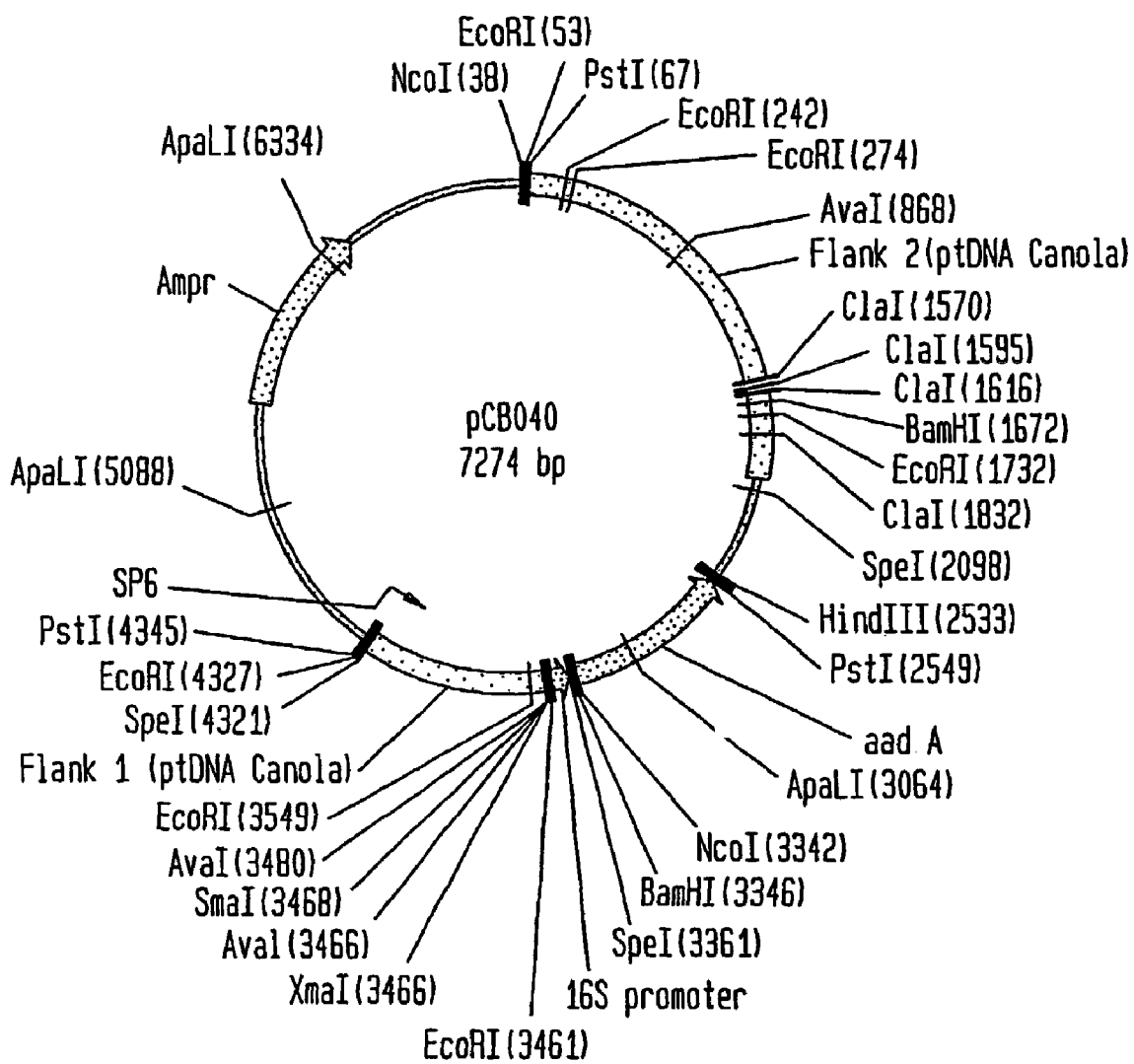
FIG. 6 is a map of plasmid pCB040 that is similar to pCB033 but in which the flanking region is selected for integration by homologous recombination into *Brassica* species.

Colonies were selected on LB-agar petri dishes containing ampicillin (75 mg/L) and spectinomycin (100 mg/L). Restriction analysis with Cfr42I, Eco32I, NotI and PvuI was used to identify positive clones and to analyse the orientation of the insert. A clone showing the correct insert was named pCB040, schematically illustrated in FIG. 6.

INDUSTRIAL APPLICABILITY

All patent and non-patent publications cited in this specification are indicative of the level of skill of those skilled in the art to which this invention pertains. All these publications and patent applications are herein incorporated by reference to the same extent as if each individual publication or patent application were specifically and individually indicated to be incorporated by reference.

The invention claimed is:

1. A method of transforming plastids, wherein the method comprises:
(a) fusing a protoplast derived from a cell of a first plant with a protoplast derived from a cell of a second plant, whereby a plastid of the cell of the first plant is transferred to the protoplast derived from the cell of the second plant, wherein said second plant is a mutant of the same species as the first plant or a member of a different species, genus or family than the first plant;
(b) introducing a nucleic acid of interest into said plastid, thus producing a transformed plastid in the cell of the second plant; and
(c) fusing the protoplast derived from the cell of the second plant with a protoplast derived from a cell of a third plant, whereby the transformed plastid is transferred to the protoplast derived from the cell of the third plant,
wherein the first and third plants are genetically identical or distinct from each other.

2. The method of claim 1, wherein the first, second and third plants are members of the same family.

3. A method of transforming plastids, wherein the method comprises:
(a) fusing a protoplast derived from a cell of a first plant with a protoplast derived from a cell of a second plants, whereby a plastid of the cell of the first plant is transferred to the protoplast derived from the cell of the second plant, wherein said second plant is a mutant of the same species as the first plant or a member of a different species, genus or family than the first plant, and wherein said plastid becomes genetically recombined with a plastid of said second plant, thus producing a recombinant plastid;
(b) introducing a nucleic acid of interest into said recombinant plastid, thus producing a transformed plastid; and
(c) fusing the protoplast derived from the cell of the second plant containing the transformed recombinant plastid with a protoplast derived from a cell of a third plant, whereby the transformed plastid is transferred to the protoplast derived from the cell of the third plant, wherein the first and third plants are genetically identical or distinct from each other.

4. The method of claim 1, wherein the second plant is a *Nicotiana* plant.

5. The method of claim 1 or 3, wherein said second plant is a *Solanum* plant.

6. The method of claim 1 or 3, wherein said second plant is a *Orychophragmus* plant.

7. The method of claim 1 or 3, wherein said second plant is a *Lesquerella* plant.

8. The method of claim 1 or 3, wherein said second plant is a *Brassica*.

9. The method of claim 1 or 3, wherein said first plant is a potato plant.

10. The method of claim 1 or 3, wherein said first plant is a tomato plant.

11. The method of claim 1 or 3, wherein said first plant is an eggplant plant.

12. The method of claim 1 or 3, wherein said first plant is a *Licium* plant.

13. The method of claim 1 or 3, wherein said first plant is a *Brassica* plant.

14. The method of claim 1 or 3, wherein said first and second plants, said first and third plants, or said first, second and third plants are members of the Gramineae family.

15. A method of making a transplastomic plant, wherein the method comprises:
(a) fusing a protoplast derived from a cell of a first plant with a protoplast derived from a cell of a second plant whereby a plastid of the cell of the first plant is transferred to the protoplast derived from the cell of the second plant, wherein said second plant is a mutant of the same species as the first plant or a member of a different species, genus or family than the first plant;
(b) introducing a nucleic acid of interest that includes a selectable marker gene into said, thus producing a transformed plastid in the cell of the second plant;
(c) fusing the protoplast derived from the cell of the second plant plastid with a protoplast derived from a cell of a third plant, whereby the transformed plastid is transferred to the protoplast derived from the cell of the third plant, and wherein the first and third plants are genetically identical or distinct from each other; and
(d) regenerating a transplastomic plant from a cell of the third plant in (c) that expresses the selectable marker gene.

16. The method of claim 15, wherein said third plant is a crop plant.

17. A method for transforming plastids, wherein the method comprises:
(a) introducing a nucleic acid of interest into a plastid of a protoplast derived from a cell of a first plant, thus producing a transformed plastid; and
(b) fusing the protoplast derived from the cell of the first plant containing the transformed plastid with a protoplast derived from a cell of a second plant, whereby the transformed plastid is transferred to the protoplast derived from the cell of the second plant, wherein said second plant is a mutant of the same species as the first plant or a member of a different species, genus or family than the first plant.

18. The method of claim 17, wherein said first and second plants are members of the same family.

19. The method of claim 17, wherein said first and second plants are species within the same genus.

20. A method for preparing a transplastomic plant, wherein the method comprises:
(a) introducing a nucleic acid of interest including a selectable marker gene into a plastid of a protoplast derived from a cell of a first plant, thus producing a transformed plastid;
(b) fusing the protoplast derived from a cell of a first plant containing the transformed plastid with a protoplast derived from a cell of a second plant whereby the transformed plastid is transferred to the protoplast derived from the cell of the second plant, wherein said second plant is a mutant of the same species as the first plant or a member of a different species, genus or family than the first plant; and
(c) regenerating a transplastomic plant from a cell of the second plant in (b) that expresses the selectable marker gene.

21. A method of transforming plastids, wherein the method comprises:
(a) fusing a protoplast derived from a cell of a first plant with a protoplast derived from a cell of a second plant, thus forming a cybrid, and wherein said second plant is a mutant of the same species as the first plant or a member of a different species, genus or family than the first plant;
(b) introducing a nucleic acid of interest into said plastid, thus producing a transformed plastid in said cybrid; and
(c) fusing said cybrid with a protoplast derived from a cell of a third plant, wherein the first and third plants are genetically identical or distinct from each other.

22. A method of transforming plastids, wherein the method comprises:
(a) transferring a plastid from a cell of a first plant to a cell of a second plant, wherein said second plant is a member of a different species, genus or family than the first plant;
(b) introducing a nucleic acid of interest into the transferred plastid, thus producing a transformed plastid; and
(c) transferring said transformed plastid into a cell of a third plant,
wherein said transferring in (a) is accomplished by sexual crossing, and wherein the first and third plants are genetically identical or distinct from each other.

* * * * *

UNITED STATES PATENT AND TRADEMARK OFFICE
CERTIFICATE OF CORRECTION

| | |
|---|---|
| PATENT NO. | : 7,226,787 B2 |
| APPLICATION NO. | : 10/239471 |
| DATED | : June 5, 2007 |
| INVENTOR(S) | : Nikolay V. Kuchuk |

It is certified that error appears in the above-identified patent and that said Letters Patent is hereby corrected as shown below:

Column 1, line 10, "TECHNICAL FIELD" should read --FIELD OF THE INVENTION--.

Column 4, line 33, "BEST MODE OF CARRYING OUT THE INVENTION" should read --DETAILED DESCRIPTION OF THE INVENTION--.

Column 11, line 25 "with a somatic cells from canola line." should read --with somatic cells from canola line.--.

Column 12, line 22, "fragment was the gel" should read --fragment was then gel--.

Column 12, at the end of line 57, insert --(SEQ ID NO: 5)--.

Column 12, at the end of line 59, insert --(SEQ ID NO: 6)--.

Column 14, line 26, delete "INDUSTRIAL APPLICABILITY".

Claim 3, Column 17, line 6, "cell of a second plants," should read --cell of a second plant,--.

Claim 6, Column 17, line 29, "is a *Orychophragmus* plant" should read --is an *Orychophragmus* plant.--

Claim 8, Column 17, line 33, insert --plant-- at the end of the sentence.

Claim 15, Column 17, line 57, "selectable marker gene into said," should read --selectable marker gene into said plastid,--.

UNITED STATES PATENT AND TRADEMARK OFFICE
CERTIFICATE OF CORRECTION

PATENT NO. : 7,226,787 B2
APPLICATION NO. : 10/239471
DATED : June 5, 2007
INVENTOR(S) : Nikolay V. Kuchuk It is certified that error appears in the above-identified patent and that said Letters Patent is hereby corrected as shown below:

Claim 15, Column 17, line 60, "second plant plastid with a protoplast" should read --second plant with a protoplast--.

Signed and Sealed this

Twenty-third Day of October, 2007

JON W. DUDAS
*Director of the United States Patent and Trademark Office*